(12) United States Patent
Ueda et al.

(10) Patent No.: US 7,556,626 B2
(45) Date of Patent: Jul. 7, 2009

(54) MEDICAL INSTRUMENT HOLDING APPARATUS

(75) Inventors: Masaaki Ueda, Sagamihara (JP); Satoshi Otsuka, Mitaka (JP); Tomoaki Yamashita, Hachioji (JP); Hisao Isobe, Hachioji (JP); Kenji Hirose, Hachioji (JP); Toru Shinmura, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/751,565

(22) Filed: Jan. 5, 2004

(65) Prior Publication Data

US 2004/0138524 A1     Jul. 15, 2004

(30) Foreign Application Priority Data

Jan. 7, 2003     (JP) .............................. 2003-001461

(51) Int. Cl.
*A61B 17/00* (2006.01)
(52) U.S. Cl. .......................................... 606/1; 600/102
(58) Field of Classification Search .............. 248/122.1; 359/377; 606/1, 130; 600/102
See application file for complete search history.

(56) References Cited

U.S. PATENT DOCUMENTS

| | | | | |
|---|---|---|---|---|
| 3,762,796 A | * | 10/1973 | Heller ........................ | 359/375 |
| 3,762,797 A | * | 10/1973 | Heller ........................ | 359/375 |
| 4,339,100 A | * | 7/1982 | Heller et al. ............. | 248/123.2 |
| 4,344,595 A | * | 8/1982 | Heller et al. ................ | 248/542 |
| 4,364,535 A | * | 12/1982 | Itoh et al. ................. | 248/123.2 |
| 4,548,373 A | * | 10/1985 | Komura ..................... | 248/122.1 |
| 4,867,405 A | * | 9/1989 | Nakamura ............. | 248/281.11 |
| 5,173,802 A | * | 12/1992 | Heller ........................ | 359/384 |
| 5,173,803 A | * | 12/1992 | Heller ........................ | 359/384 |
| 5,257,998 A | * | 11/1993 | Ota et al. ..................... | 606/130 |
| 5,609,565 A | | 3/1997 | Nakamura | |
| 5,667,186 A | * | 9/1997 | Luber et al. .................. | 248/550 |
| 5,825,536 A | * | 10/1998 | Yasunaga et al. ............ | 359/384 |
| 5,957,423 A | * | 9/1999 | Kronner ................... | 248/278.1 |
| 6,045,104 A | * | 4/2000 | Nakamura et al. ...... | 248/280.11 |
| 6,050,530 A | * | 4/2000 | Nakamura ................ | 248/123.2 |
| 6,514,239 B2 | | 2/2003 | Shimmura et al. | |
| 6,833,950 B2 | * | 12/2004 | Schmidt ..................... | 359/384 |
| 6,899,307 B2 | * | 5/2005 | Strauss et al. .......... | 248/280.11 |

(Continued)

FOREIGN PATENT DOCUMENTS

JP          7-227398          8/1995

(Continued)

*Primary Examiner*—Ahmed M Farah
(74) *Attorney, Agent, or Firm*—Scully, Scott, Murphy & Presser, P.C.

(57) ABSTRACT

A medical instrument holding apparatus includes a supporting mechanism, a moving mechanism, a basal portion and a counterweight. The supporting mechanism supports a medical instrument. The moving mechanism which has first and second sides, and a shaft portion located between the first and second sides. The moving mechanism supports the supporting mechanism, allowing the medical instrument and the supporting mechanism to be moved around the shaft portion. The basal portion is coupled to the shaft portion. The basal portion supports the moving mechanism, allowing the moving mechanism to rotate around the shaft portion. The counterweight is located on the second side of the moving mechanism. The counterweight generates a first rotation moment being smaller than a second rotation moment generated from the weights of the medical instrument and the supporting mechanism and acting around the shaft portion in the opposite direction to the second rotation moment.

7 Claims, 4 Drawing Sheets

U.S. PATENT DOCUMENTS

| | | | |
|---|---|---|---|
| 2001/0027313 A1* | 10/2001 | Shimmura et al. | 606/1 |
| 2004/0172012 A1* | 9/2004 | Otsuka et al. | 606/1 |

FOREIGN PATENT DOCUMENTS

| | | | |
|---|---|---|---|
| JP | 2000-245738 | 9/2000 | |
| JP | 2001-258903 | 9/2001 | |
| JP | 2001-299695 | 10/2001 | |
| JP | 2001-95819 | 4/2004 | |

* cited by examiner

MEDICAL INSTRUMENT HOLDING APPARATUS

CROSS-REFERENCE TO RELATED APPLICATIONS

This application is based upon and claims the benefit of priority from the prior Japanese Patent Application No. 2003-001461, filed Jan. 7, 2003, the entire contents of which are incorporated herein by reference.

BACKGROUND OF THE INVENTION

1. Field of the Invention

The present invention relates to a medical instrument holding apparatus for holding medical instruments, such as endoscopes, surgical instruments, etc., that are used in the surgical removal of tumors in the field of neurosurgery, for example.

2. Description of the Related Art

Modern microsurgery is being frequently performed using operating microscopes for extended observation of fine sites of neurosurgical operations. The observation range of an operating microscope is limited to regions that can be observed through an opening in the cranium. These regions involve dead-angle portions that cannot be viewed through the operating microscope. An endoscope is used to observe these dead-angle portions.

In performing microsurgery, an operator watches an observational image of the endoscope as he/she inserts a surgical instrument into a region to be treated in the cranium. As this is done, the endoscope is supported and fixed by means of a medical instrument holding apparatus that has a plurality of arms and joint portions. Important tissues, such as nerves, blood vessels, etc., are intertwined intricately and minutely in the cranium. Therefore, the endoscope is expected to be designed so that it can be moved finely and smoothly and fixed in a correct position by means of the holding apparatus.

Described in U.S. Pat. No. 5,609,565, for example, is a medical instrument holding apparatus that has a holding portion on its distal end for holding a medical instrument, such as an endoscope. This apparatus has ball joints for joint portions of a plurality of arms and a counterbalance or counterweight on the side opposite the distal end portion that holds the medical instrument. The counterweight is balanced with the medical instrument and the like. Thus, the operator can freely locate the medical instrument in a desired position with a small force. In this apparatus, the joints of the arms are composed of ball joints that can move in the same manner as those of the human body, for example. In consequence, the operator can use the ball joints to operate the medical instrument on the holding portion with a natural feeling of manipulation. Further, the operator can locate the medical instrument in an optimum position, depending on the technique or the site of operation.

Described in Jpn. Pat. Appln. KOKAI Publication No. 7-227398, for example, is a medical instrument holding apparatus in which each of arms that constitute a body-supporting portion is composed of a parallelogrammatic link. In this apparatus, the center of gravity of a medical instrument that is attached to the distal end portion of the supporting portion is aligned with the center of inclination of an L-shaped arm end portion. This apparatus is provided with two counterweights on the side of the body-supporting portion opposite from the side on which the medical instrument is located. The counterweights serve to cancel the weight of the medical instrument and the like. By using the apparatus constructed in this manner, the operator can continually maintain the balanced state of the medical instrument on the distal end portion of the body supporting portion or parallelogrammatic link structure as he/she moves the instrument by means of the counterbalanced arms of the supporting portion. Thus, the operator can easily perform fine adjustment such as the change of the endoscopic field.

BRIEF SUMMARY OF THE INVENTION

A medical instrument holding apparatus according to an aspect of the invention includes a supporting mechanism, a moving mechanism, a basal portion and a counterweight. The supporting mechanism supports a medical instrument. The moving mechanism which has first and second sides, and a shaft portion located between the first and second sides. The moving mechanism supports the supporting mechanism, allowing the medical instrument and the supporting mechanism to be moved around the shaft portion. The basal portion is coupled to the shaft portion. The basal portion supports the moving mechanism, allowing the moving mechanism to rotate around the shaft portion. The counterweight is located on the second side of the moving mechanism. The counterweight generates a first rotation moment being smaller than a second rotation moment generated from the weights of the medical instrument and the supporting mechanism and acting around the shaft portion in the opposite direction to the second rotation moment.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Preferred embodiments of the present invention will now be described with reference to the accompanying drawings.

A first embodiment will first be described with reference to FIGS. 1 and 2.

Figure 1:
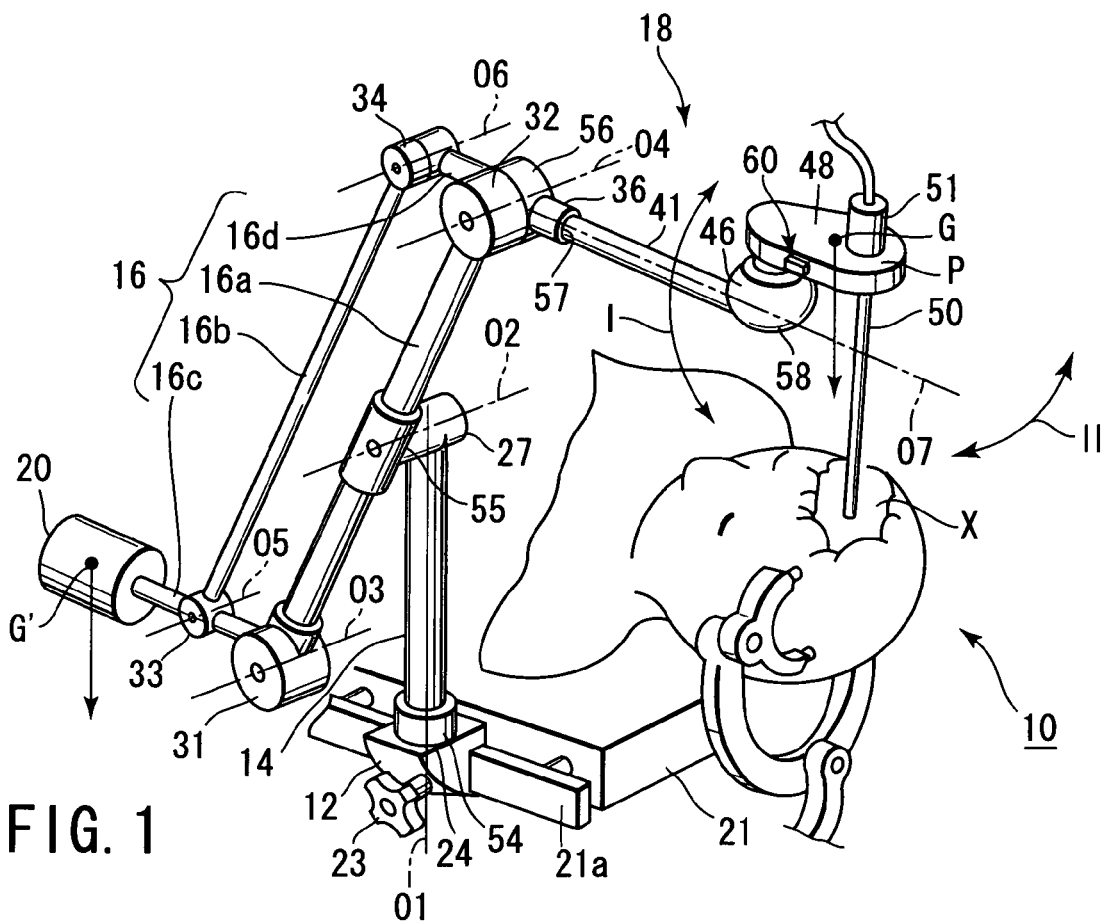
FIG. 1 is a schematic view showing the general system configuration of a medical instrument holding apparatus according to a first embodiment of the invention.

As shown in FIG. 1, a medical instrument holding apparatus 10 according to this embodiment comprises a basal portion (base 12 and support arm 14), moving mechanism (parallelogrammatic link mechanism 16), medical instrument supporting mechanism 18, and counterweight or counterbalance 20.

The base 12 is movable along a side rail 21a that is attached to the flank of an operating table 21. The base 12 is fixed in a desired position on the side rail 21a by means of a fixing screw 23, for example. As shown in FIGS. 1 and 2, a bearing 24 is attached to the base 12. The lower end of the support arm 14 is supported on the bearing 24 so that the arm 14 is rotatable around a vertical axis O1 with respect to the base 12.

A bearing or supporting portion 27 is attached to the upper end of the support arm 14. The bearing 27 has an axis O2 of rotation that extends at right angles to the vertical axis O1. The parallelogrammatic link mechanism 16 is set on the axis O2 for rotating or swinging motion. The link mechanism 16 is provided with first, second, third, and fourth arms 16a, 16b, 16c and 16d and first, second, third, and fourth bearings 31, 32, 33 and 34.

The first arm 16a is a rotating member that is supported by means of the bearing 27. The bearing 27 is located on a substantially central part of the first arm 16a. Alternatively, the bearing 27 may be provided on each end of the first arm 16a or in any position between its opposite ends. The first bearing 31 and the second bearing 32 are located on one end (lower end) and the other end (upper end), respectively, of the first arm 16a. The first bearing 31 has an axis O3 of rotation that extends parallel to the axis O2. The second bearing 32 has an axis O4 that extends parallel to the axis O2. The respective parallel axes O3 and O4 of the first and second bearings 31 and 32 are connected with the respective one-ends (right-hand ends in FIGS. 1 and 2) of the third and fourth arms 16c and 16d that are rotatable around the axes O3 and O4, respectively.

The third and fourth bearings 33 and 34 are located on the other end side (left-hand end side) of the third arm 16c and the other end (left-hand end) of the fourth arm 16d, respectively. The third bearing 33 has an axis O5 of rotation that extends parallel to the axis O2. The fourth bearing 34 has an axis O6 that extends parallel to the axis O2. The third bearing 33 is tied with the second arm 16b that is rotatable around the axis O5 and extends parallel to the first arm 16a.

The parallelogrammatic link mechanism 16 is constructed in this manner. It can be transformed within a given range by means of the first to fourth bearings 31 to 34 with the first and third arms 16a and 16c kept parallel to the second and fourth arms 16b and 16d, respectively.

The third arm 16c is longer than the fourth arm 16d. The other end of the third arm 16c extends outside the parallelogrammatic link mechanism 16. The distance between the first and second bearings 31 and 32 on the end portions of the first arm 16a and the distance between the third and fourth bearings 33 and 34 on the end portions of the second arm 16b are longer than the distance between the first and third bearings 31 and 33 of the third arm 16c that is connected to the first and third bearings 31 and 33.

The second bearing 32 of the parallelogrammatic link mechanism 16 is fitted with a fifth bearing 36 having an axis O7 that extends at right angles to the axis O4 of the second bearing 32. The fifth bearing 36 is provided with an elongate inclinable support arm 41, tilting-supporting mechanism, and holding mechanism, which constitutes the medical instrument supporting mechanism. The supporting mechanism supports a medical instrument, such as an endoscope 50, in an inclinable manner. One end (proximal end) of the support arm 41 is supported on the fifth bearing 36. The one end of the support arm 41 and the one end of the fourth arm 16d are joined together and coaxially located on the axis O7. A ball joint 46 is mounted on the other end (distal end) or the support arm 41. The ball joint 46 is a tilting-supporting mechanism that supports the holding mechanism so that the holding mechanism can be inclined in the directions indicated by arrows I and II in FIG. 1. The holding mechanism for holding the medical instrument is supported on the ball joint 46.

In this embodiment, one end of a holding arm 48 for use as the holding mechanism is supported on the ball joint 46. The medical instrument or endoscope 50 is attached to the other end of the arm 48. A TV camera 51 for picking up an observational image of the endoscope 50 is connected optically to the endoscope. The camera 51 is connected electrically to a camera control unit (not shown). The camera control unit is connected electrically to a TV monitor (not shown).

The counterweight 20 is removably attached to the other end of the third arm 16c that extends outward from the third bearing 33, which is diagonal to the second bearing 32. The counterweight 20 has an optional weight to cancel the moment of inertia (rotation moment) that is generated around the axis O2 by the gravity of a heavy structure that combines the holding arm 48, endoscope 50, TV camera 51, etc. The weight of the counterweight 20 is suitably selected depending on the gravity of the heavy structure and the distance from the axis O2. Thus, the rotation moment around the axis O2 can be suitably increased or decreased.

The bearing 24 is fitted with a first electromagnetic brake or clutch 54 that electrically regulates the rotating motion of the support arm 14 around the axis O1 with respect to the base 12. The bearing 27 is fitted with a second electromagnetic brake 55 that electrically regulates the rotating motion of the first arm 16a around the axis O2. The second bearing 32 is fitted with a third electromagnetic brake 56 that electrically regulates the rotating motion of the fourth arm 16d around the axis O3. The fifth bearing 36 is fitted with a fourth electromagnetic brake 57 that electrically regulates the rotating motion of the inclinable support arm 41 around the axis O4. A fifth electromagnetic brake 58 is located in the ball joint 46. The fifth electromagnetic brake 58 electrically regulates the inclination of the holding arm 48 in the directions indicated by arrows I and II.

The holding arm 48 is fitted with an input or push-button switch 60 for use as an input switching mechanism. When the switch 60 is depressed, it changes the operating state of the first to fifth electromagnetic brakes 54 to 58 from a locked state to an unlocked state. The input switch 60 is connected to a control circuit (not shown) as a control mechanism, which controls a signal that is generated when an operator depresses the switch 60.

Thus, when the first to fifth electromagnetic brakes 54 to 58 are in the unlocked state, the first and second arms 16a and 16b and the third and fourth arms 16c and 16d can be rotated around the first to fourth bearings 31 to 34 without failing to maintain their parallel relationship. In this way, the parallelogrammatic link mechanism 16 can be transformed to move the holding arm 48, ball joint 46, and inclinable support arm 41 within given ranges. Thus, the link mechanism 16 is a moving or balancing mechanism that moves the endoscope 50 on the distal end of the holding arm 48 in a balanced state within a given range.

Figure 2:
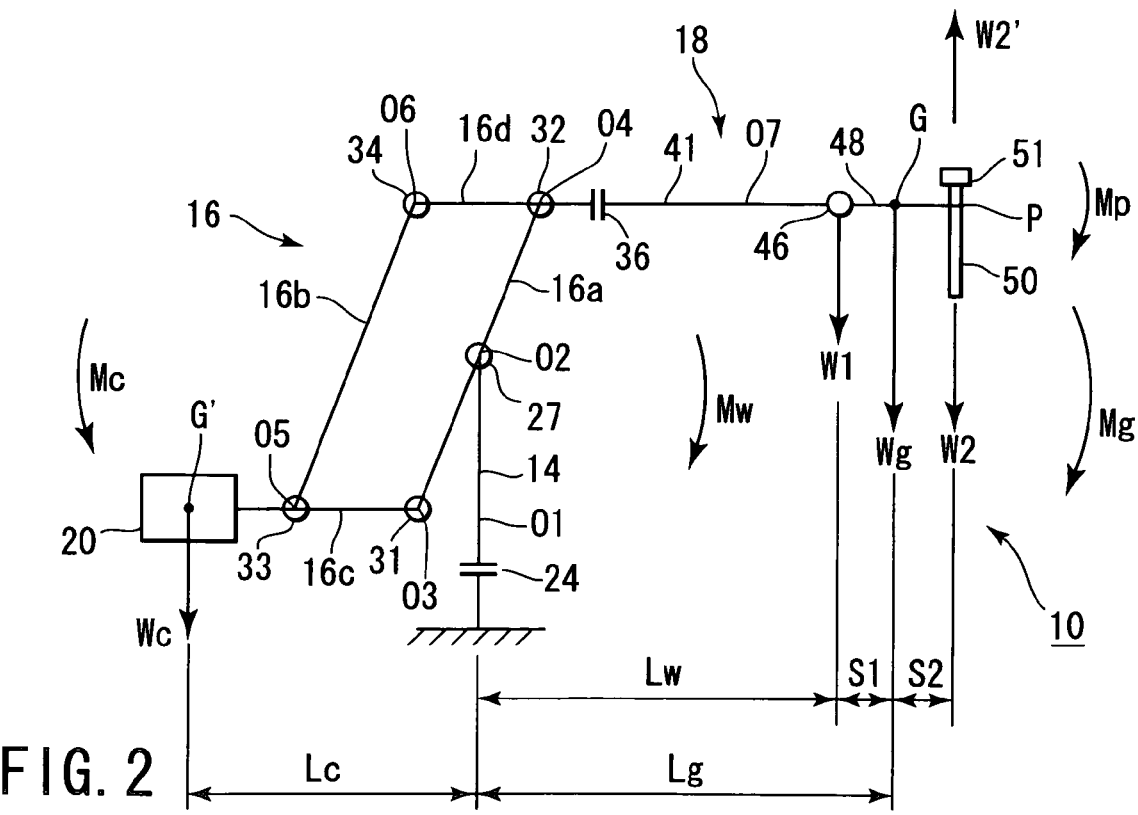
FIG. 2 is a diagram showing the balance of the holding apparatus of the first embodiment.

In FIGS. 1 and 2, symbol G designates the center of gravity of the heavy structure including the medical instrument holding arm 48, endoscope 50, and TV camera 51 that are supported on the inclinable support arm 41 by means of the ball joint 46 in the aforesaid manner. Symbol G' designates the center of gravity of the counterweight 20. Symbol P designates the center or the point of action of a grip section of the endoscope 50 that is held by the operator who moves the endoscope.

The weight of the counterweight 20, compared to that of the heavy structure, including the medical instrument holding arm 48, endoscope 50, TV camera 51, etc., that is, the way of balancing, will now be described with reference to FIG. 2. The respective weights of the inclinable support arm 41 and the first to fourth arms 16a to 16d that constitute the parallelogrammatic link mechanism 16 are smaller enough than those of the counterweight 20 and the heavy structure, including the medical instrument holding arm 48, endoscope 50, TV camera 51, etc. In the description to follow, therefore, the respective weights of the support arm 41 and the arms 16a to 16d are ignored or supposed to be zero.

If the weight of the heavy structure on the center G of gravity and the distance from the center G to the axis O1 that is perpendicular to the axis O2 of the bearing 27 are Wg and Lg, respectively, a rotation moment Mg around the axis O2 that is generated at the center G is $$Mg = Wg \cdot Lg. \tag{1}$$

If the point P of action is set on the center of the grip section of the endoscope 50 that is held by the operator who moves the endoscope 50, the operator bears a part of the weight Wg that acts of the center G of gravity when he/she operates the endoscope 50. If the weight that acts on the ball joint 46 with the holding arm 48 held by the operator and the magnitude of retention or operating power of the operator are W1 and W2', respectively, Wg is $$Wg = W1 - W2'. \tag{2}$$

If the weight W2 that acts on the point P of action is regarded as a force of reaction to the retention W2' (W2=−W2'), equation (2) can be rearranged as follows:

$$Wg = W1 + W2. \tag{3}$$

Let it be supposed that the distance from the center of the ball joint 46 to the center G of gravity and the distance from the center G to the point P of action are S1 and S2, respectively. Thus, the point P of operation of the endoscope 50 is supposed to be at a distance of S1+S2 from the center of inclination of the ball joint 46 in the lateral and longitudinal directions. Based on a moment of inertia around the center G, W2 is given by $$W2 = (S1/S2) \cdot W1. \tag{4}$$

From equations (3) and (4), we obtain $$W1 = (S2/(S1+S2)) \cdot Wg. \tag{5}$$

A moment Mw of inertia around the axis O2 of the bearing 27 that is generated in the center of the ball joint 46 is given by $$Mw = W1 \cdot Lw. \tag{6}$$

where Lw is the distance from the axes O1, O2 to the weight W1.

On the other hand, a rotation moment Mc around the axis O2 that is generated by the counterweight 20 is given by $$Mc = Wc \cdot Lc, \tag{7}$$

where Wc is the weight of the counterweight 20, and Lc is the distance from the center G' of gravity of the counterweight 20 to the axes O1 and O2 In this embodiment, the weight Wc of the counterweight 20 is adjusted to a value that cancels the moment Mw, so that we have Mw=Mc. Based on equations (6) and (7), the weight Wc of the counterweight 20 is given by $$Wc = (Lw/Lc)(S2/(S1+S2)) \cdot Wg. \tag{8}$$

The distance from the axis O2 to the counterweight 20 and the weight of the counterweight are set so that the above relationship is established.

Let it be supposed that the ratio between the distances Lw and Lc from the axis O2 is Lw:Lc=2:1 and that the ratio between the distances S1 and S2 from the center G of gravity is S1:S2=1:1, for example. The first to fourth arms 16a to 16d, inclinable support arm 41, and holding arm 48 are supposed to be formed so that those relations are established. The respective weights Wc and Wg of the counterweight 20 and the heavy structure have a relationship, $$Wc = Wg. \tag{9}$$

If we have Lw=Lg=2, the rotation moment Mc around the axis O2 that is generated by the counterweight 20 and the rotation moment Mg around the axis O2 that is generated in the position of the center G of gravity of the heavy structure given by $$Mc = Wg \cdot Lc = Wg, \tag{10}$$

$$Mg = Wg \cdot Lg = 2Wg, \tag{11}$$

respectively. Based on equations (10) and (11), the relationship between the rotation moment Mc around the axis O2 that is generated by the counterweight 20 and the rotation moment Mg around the axis O2 that is generated in the center G of gravity is given by Mc=(½)Mg. Accordingly, the distances Lw, Lc, S1 and S2 and the weights Wc and Wg are set so that the above relationship between the moments is established, whereby the counterweight 20 and the heavy structure are balanced with each other.

The following is a description of the operation of the medical instrument holding apparatus 10 constructed in this manner.

As shown in FIG. 1, the operator holds the endoscope 50 in a hand as he/she depresses the input switch 60 on the holding arm 48 with a finger or the palm of the holding hand, in order to insert the endoscope into a site X of operation to observe the site X internally. The first to fifth electromagnetic brakes 54 to 58 are unlocked by means of the control circuit (not shown). Thus, the support arm 14 is allowed to rotate around the axis O1. As the first arm 16a is allowed to rotate around the axis O2, the whole parallelogrammatic link mechanism 16 tilts around the axis O1. As the fourth arm 16d is allowed to rotate around the axis O4 of the second bearing 32, the link mechanism 16 is transformed, whereupon the inclinable support arm 41 is allowed to move. Thereupon, the support arm 41 is allowed to rotate around the axis O7, and the holding arm 48 is allowed to tilt in the directions indicated by arrows I and II in FIG. 1 by means of the ball joint 46. Thus, the operator can three-dimensionally locate the distal end portion of the endoscope 50 in a free position.

The operator manually holds the point P of action of the endoscope 50 as he/she moves the endoscope 50. The weight Wg of the heavy structure, including the medical instrument holding arm 48, endoscope 50, TV camera 51, etc., produces a rotation moment Mp around the center of the ball joint 46. The weight W2, a part of the weight Wg, acts as a force of unbalance on the operator's hand. Thus, the operator works the reaction force W2' in the direction opposite to the weight W2 the point P of action in order to support the force of unbalance manually. Since the weight W2 and the reaction force W2' cancel each other (W2=W2'), the weight W1 that acts on the ball joint 46 is W1=Wg−W2+W2'=Wg. Therefore, the rotation moment around the axis O2 is influenced only by the weight W1 that acts on the ball joint 46 (Wg=W1). Thus, the moment Mw of inertia around the axis O2 of the bearing 27 that is generated in the center of the ball joint 46 is equal to the value given by equation (6).

The rotation moment Mc around the axis O2 that is generated by the counterweight 20 is adjusted to a weight that generates a rotation moment to cancel the moment Mw (Mc=Mw). To attain this, the operator sets the parallelogrammatic link mechanism 16 and the inclinable support arm 14 so that the relationship given by equation (8) is established. Thus, the operator moves the endoscope 50 toward a desired position with the apparatus 10 balanced and locates the endoscope 50 in the desired position. Since the apparatus 10 is balanced in this manner, the operator can move the endoscope 50 toward and locate it in the desired position with a small force.

After locating the endoscope 50 in the desired position, the operator releases the input switch 60 from his/her finger's press, thereby bringing the first to fifth electromagnetic brakes 54 to 58 to the locked state. Thereupon, their corresponding bearings 24, 27, 32, 36 and 46 are fixed, so that the endoscope 50 is securely fixed in the desired position. An observational image of the site X of operation that is relayed through an optical system (not shown) of the endoscope 50 is picked up by means of the TV camera 51, then displayed on the monitor by means of a TV control unit (not shown), and observed by the operator.

According to this embodiment described above, the following effects can be obtained.

The ball joint 46 that tilts the endoscope 50 in the lateral and longitudinal directions and the point P of action of the endoscope 50 are not coincident with each other. Therefore, the grip section or control section of the endoscope 50 that is held by means of the holding arm 48 may be made substantially as large as the eyepiece of a conventional endoscope and the TV camera. In consequence, the ball joint 46 and the endoscope 50 never interfere with each other, so that no extra device is needed. Thus, the arrangement of this embodiment ensures a working space substantially as wide as the space for the case where the holding arm 48 is not used, that is, the medical instrument 50 is connected directly to the inclinable support arm 41.

The weight of the counterweight 20 for the parallelogrammatic link mechanism 16 is set so that it is balanced with a weight from which the force of unbalance around the ball joint 46 is subtracted. Accordingly, the operator can balance the apparatus 10 only by supporting the weight W2 that acts on the point P of action with the force of unbalance that acts on the distal end side of the distal joint or ball joint 46 of the inclinable support arm 41, that is, the force W2' of reaction to the weight W2. Thus, the endoscope 50 can be freely located in the desired position with a small force with the first to fifth electromagnetic brakes 54 to 58 unlocked.

The inclinable support arm 41 supports only the holding arm 48 by means of the ball joint 46. The force of unbalance is settled in a single direction, such as a vertical direction, in which the holding arm 48 and the medical instrument 50 weigh. If the first to fifth electromagnetic brakes 54 to 58 are unlocked, therefore, the arms cannot easily move in undesired directions. Thus, fine manipulation of the instrument 50 can be stabilized, for example.

According to the medical instrument holding apparatus 10 of this embodiment, restrictions on the observation of the site of operation and the operating space for the medical instrument 50 can be minimized. Thus, the instrument 50 can be moved and fixed easily and securely, so that its fine manipulation, for example, can be stabilized.

Although the endoscope 50 has been described as an example of the medical instrument according to this embodiment, the same effect can be obtained with use of any other suitable tool such as a forceps or cutter.

A second embodiment will now be described with reference to FIGS. 3 to 5. This embodiment is a modification of the first embodiment. Like reference numerals are used to designate like members of the first and second embodiments, and a detailed description of those members is omitted.

A grip 70 is used in place of the holding arm 48 (see FIG. 1) as the holding mechanism. A counterweight adjusting mechanism 72 is used in place of the attached counterweight 20 (see FIG. 1).

Figure 3:
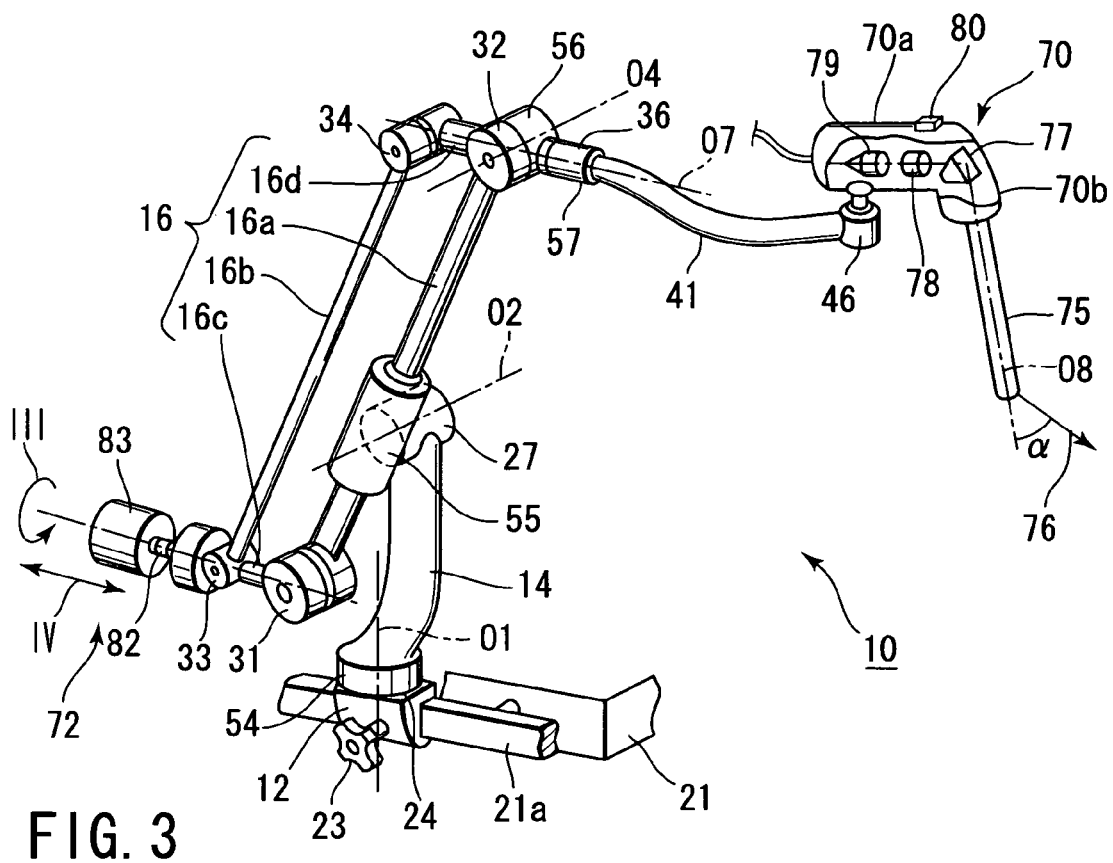
FIG. 3 is a schematic view showing the general system configuration of a medical instrument holding apparatus according to a second embodiment of the invention.
Figure 4:
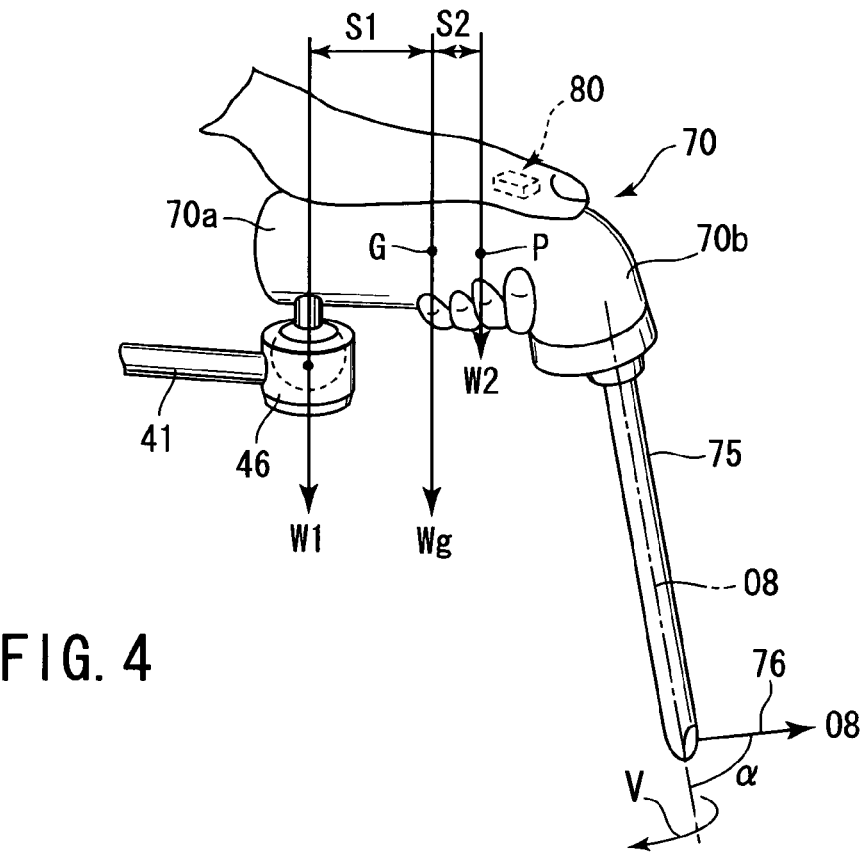
FIG. 4 is a schematic view showing the way an operator holds a medical instrument attached to the holding apparatus of the second embodiment shown in FIG. 3.

As shown in FIGS. 3 and 4, instead of the holding arm 48 used in the first embodiment, the grip 70 for holding a medical instrument is rotatably mounted on a ball joint 46 that is attached to the distal end of an inclinable support arm 41. The grip 70 has a body portion 70a, which is rotatably mounted on the ball joint 46, and a bent portion 70b. The bent portion 70b is bent at a suitable angle to the body portion 70a. An endoscope 75, for use as the medical instrument, for example, is held on the distal end of the bent portion 70b. The endoscope 75 is rotatably held on its axis O8 of insertion. As shown in FIGS. 3 and 4, the endoscope 75 is a so-called straboscope or lateral-view endoscope that has an observational optical axis 76 in its distal end portion. The axis 76 is inclined at a certain angle a to the axis O8. The endoscope 75 contains an objective lens, relay optical system, etc. (not shown) that are arranged along the axis O8.

As shown in FIG. 3, the grip 70 has therein a reflective member 77, relay optical system 78, and TV camera 79. These elements 77, 78 and 79 are connected optically to the relay optical system in the endoscope 75. An image transmitted through the relay optical system in the endoscope 75 is reflected by the reflective member 77 and made incident on the camera 79 via the relay optical system 78. An observational image of the endoscope 75 is formed on an image-pickup element in the camera 79 by means of the optical system 78 in the grip 70.

A switch 80 is located on the top surface of the grip 70. The switch 80 is used to lock and unlock first to fifth electromagnetic brakes 54 to 58. The switch 80 is connected to a control circuit (not shown). If the operator depresses the switch 80, the brakes 54 to 58 are unlocked. If the switch 80 is released, the brakes 54 to 58 are locked.

The counterweight adjusting mechanism 72 is located on the other end side of a third arm 16c of a parallelogrammatic link mechanism 16 that extends outside the mechanism 16. The adjusting mechanism 72 comprises a lead screw 82 and a counterweight 83. The screw 82, which is coaxial with the third arm 16c, is formed integrally on the other end portion of the arm 16c that extends outside the link mechanism 16. The lead screw 82 is fitted with the counterweight 83 that can move in the direction of arrow IV when it is rotated in the direction of arrow III. Thus, the counterweight 83 is spirally fitted on the screw 82 so that its rotation moment around an axis O2 is variable.

The following is a description of the operation of the medical instrument holding apparatus 10 constructed in this manner.

In observing a region in front of the body portion 70a of the grip 70, the operator holds the grip 70 in the manner shown in FIG. 4, for example. The operator depresses the switch 80 with the thumb of his/her holding hand, for example, and puts the forefinger on a region around the boundary between the body portion 70a and the bent portion 70b of the grip 70. FIG. 4 shows the positional relations between the center G of gravity of a heavy structure, including the endoscope 75 and the grip 70, the center of the ball joint 46, and the point P of action at which the operator holds the grip 70. When the region in front of the grip 70 is observed, the switch 80 is depressed so that the bent portion 70b and the endoscope 75 are situated ahead of the operator's hand, and the center G of gravity of the heavy structure is situated closer to the point P of action. The point P of action is situated in a substantially halfway position between the thumb and the other fingers that hold the grip 70. Symbols S1 and S2 designate the distance from the center G of gravity to the ball joint 46 and the distance from the center G to the point P of action, respectively.

If the operator depresses the switch 80 on the grip 70, the first to fifth electromagnetic brakes 54 to 58 are unlocked. As in the case of the first embodiment, the rotation moment around the axis O2 based on a weight W1 that acts on the ball joint 46 is canceled by the parallelogrammatic link mechanism 16, support arm 41, and counterweight 83 shown in FIG. 3. Thus, the operator can move the endoscope 75 to a desired position with a small force.

If the operator removes the thumb from the switch 80, the first to fifth electromagnetic brakes 54 to 58 are locked. In consequence, the endoscope 75 is fixed. Light that is incident upon the objective lens of the endoscope 75 is propagated via the relay optical system (not shown) of the endoscope 75, the reflective member 77 of the grip 70, and the relay optical system 78 and formed on the image-pickup element of the TV camera 79. The resulting observational image is displayed on a monitor (not shown). If the ratio between the distances S1 and S2 shown in FIG. 4 is S1:S2=2:1, the weight W1 that acts on the ball joint 46, based on equation (5), is $$W1=Wg/3. \tag{12}$$

The following is a description of the case where the operator uses the endoscope 75 to observe a site in a direction different from the direction shown in FIG. 4. For example, the site is observed in a direction diametrically opposite to the direction shown in FIG. 4, that is, in the direction of observation shown in FIG. 5. In this case, the endoscope 75 is rotated for about 180° in the direction indicated by arrow V (see FIG. 4) around the axis O8. As shown in FIG. 5, the operator holds the grip 70 in the direction opposite to the direction shown in FIG. 4. For example, the operator depresses the switch 80 with the thumb and puts the forefinger around the boundary between the body portion 70a and the bent portion 70b. The front side of the hand is directed toward the ball joint 46 on the proximal end side of the body portion 70a. FIG. 5 shows the positional relationships between the center G of gravity of a heavy structure, including the endoscope 75 and the grip 70, the center of the ball joint 46, and the point P of action at which the operator holds the grip 70. When the region at the back of the grip 70 is observed, the center G of gravity of the heavy structure is situated near a substantially central part of the body portion 70a of the grip 70 with the switch 80 depressed so that the endoscope 75 is located behind the hand. The point P of action is situated in a substantially halfway position between the thumb and the other fingers that hold the grip 70.

If the operator depresses the switch 80 on the grip 70, as mentioned before, the first to fifth electromagnetic brakes 54 to 58 are unlocked. As in the case of the first embodiment, the rotation moment around the axis O2 based on the weight W1 that acts on the ball joint 46 is canceled by the counterweight 83 shown in FIG. 3. Thus, the operator can move the endoscope 75 to a desired position with a small force.

Figure 5:
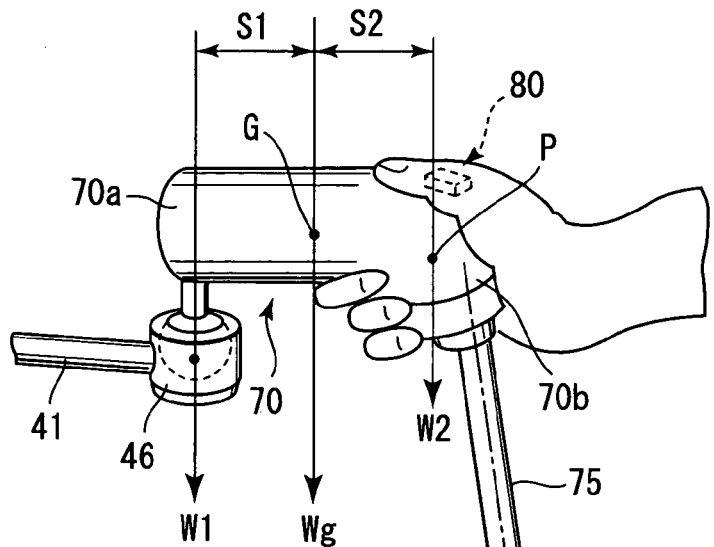
FIG. 5 is a schematic view showing the way the operator holds the medical instrument attached to the holding apparatus of the second embodiment shown in FIG. 4 from the opposite side.

If the ratio between the distances S1 and S2 shown in FIG. 5 is S1:S2=1:1, the weight W1 that acts on the ball joint 46, based on equation (5), is $$W1=Wg/2, \tag{13}$$

as mentioned before. Comparison between equations (12) and (13) indicates that the value of the weight W1 varies depending on the method of holding the grip 70.

As shown in FIG. 3, the operator rotates the counterweight 83 around its central axis or in the direction of arrow III. Thereupon, the lead screw 82 causes the counterweight 83 to rotate as it moves in the direction of arrow IV, that is, in the axial direction of the third arm 16c. If the weight W1 is increased from Wg/3 (equation (12)) to Wg/2 (equation (13)), as mentioned before, for example, the action of the counterweight 83 must be enhanced. To attain this, the counterweight 83 is rotated and moved away from the parallelogrammatic link mechanism 16 so that it is securely balanced with the weight W1.

According to this embodiment described above, the following effects can be obtained in addition to the effects described in connection with the first embodiment.

The force of unbalance, which is created by the dislocation of the point P of action that varies depending on the method and position of holding the grip 70, can be easily corrected by moving the counterweight 83 along the axis of the third arm 16c. Thus, the endoscope 75 can be operated more securely and easily.

The grip 70 has therein the relay optical system 78 and the TV camera 79 that picks up the observational image of the endoscope 75. In general, the grip 70 extends from the inclinable support arm 41 so as to be rotatable by means of the ball joint 46. Therefore, the endoscope 75 can be miniaturized without carrying any extra members around the grip section. A wider working space can be secured for the treatment of the site of operation under the observation through the endoscope 75.

In this embodiment, the grip 70 has therein the TV camera 79 and the like that conventionally project in the direction of the observational optical axis. Accordingly, the projection in the direction of the observational optical axis can be minimized. If the endoscope 75 is used in combination with an operating microscope (not shown), therefore, the endoscope 75 cannot easily become obstructive, so that its manipulability can be improved. Thus, the site of operation can be treated with higher reliability.

A third embodiment will now be described with reference to FIGS. 6 to 9. This embodiment is a modification of the second embodiment. Therefore, like reference numerals are used to designate like members of the second and third embodiments, and a detailed description of those members is omitted.

In this embodiment, a universal joint 88 is used in place of the counterweight 83 for use as the tilting-supporting mechanism described in connection with the second embodiment.

The third embodiment differs from the second embodiment also in that the adjusting mechanism 72 for the counterweight 83 is replaced with an alternative counterweight adjusting mechanism 90. The following is a description of different portions only.

Figure 6:
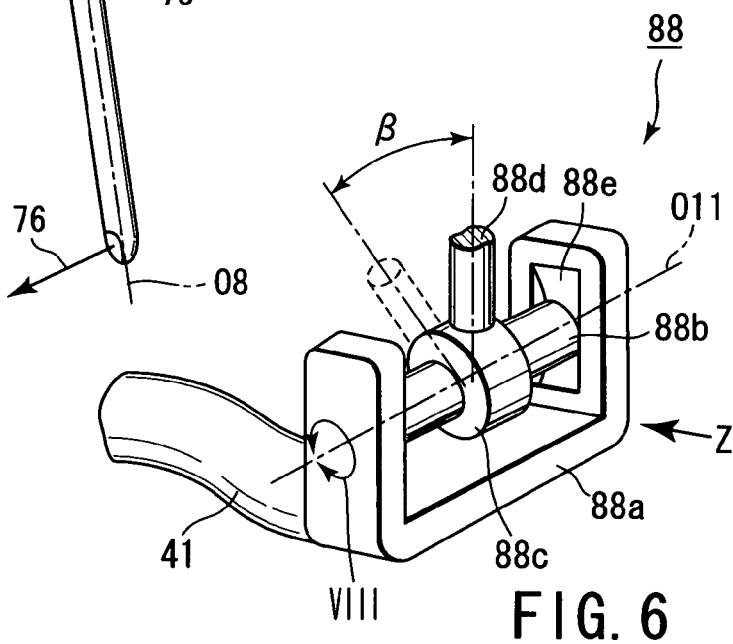
FIG. 6 is a schematic view showing a universal joint portion of a medical instrument holding apparatus according to a third embodiment.

The configuration of the universal joint 88 will be described with reference to FIGS. 6 and 7. The joint 88 comprises a bearing portion 88a, shaft member 88b, wheel 88c, and supporting member 88d. The bearing portion 88a is substantially U-shaped, for example. It is connected to the other end (right-hand end in FIG. 3) of a support arm 41. Recessed supporting portions 88e are formed individually in the opposite inner walls of the bearing portion 88a. They individually support the opposite end portions of the shaft member 88b. Each supporting portion 88e has the shape of a circumferential or spherical surface, for example. Each end portion 88f of the shaft member 88b has a shape such that the shaft member 88b can slide along its corresponding supporting portion 88e so as to be swingable or inclinable in the direction of arrow VII in FIG. 7. For example, each end portion 88f has the shape of a circumferential or hemispherical surface.

On the outer peripheral surface of the central part of the shaft member 88b, a substantially disc-shaped or columnar wheel 88c is formed integrally with the shaft member 88b. The wheel 88c rotates as the shaft member 88b rotates around its axis O11 (or in the direction of arrow VIII in FIG. 6). One end of the supporting member 88d is coupled integrally to the outer peripheral surface of the wheel 88c. The supporting member 88d has an axis that extends toward the center of the wheel 88c and at right angles to the axis O11 of the shaft member 88b. When the shaft member 88b rotates around the axis O11, the wheel 88c and the supporting member 88d rotate around the axis O11 (or in the direction of arrow VIII). The body portion 70a of the grip 70 (not shown in FIGS. 6 and 7) is attached integrally to the other end of the supporting member 88d. Thus, the grip 70 can rotate three-dimensionally within a given range as the supporting member 88d rotates or the shaft member 88b swings.

Figure 7:
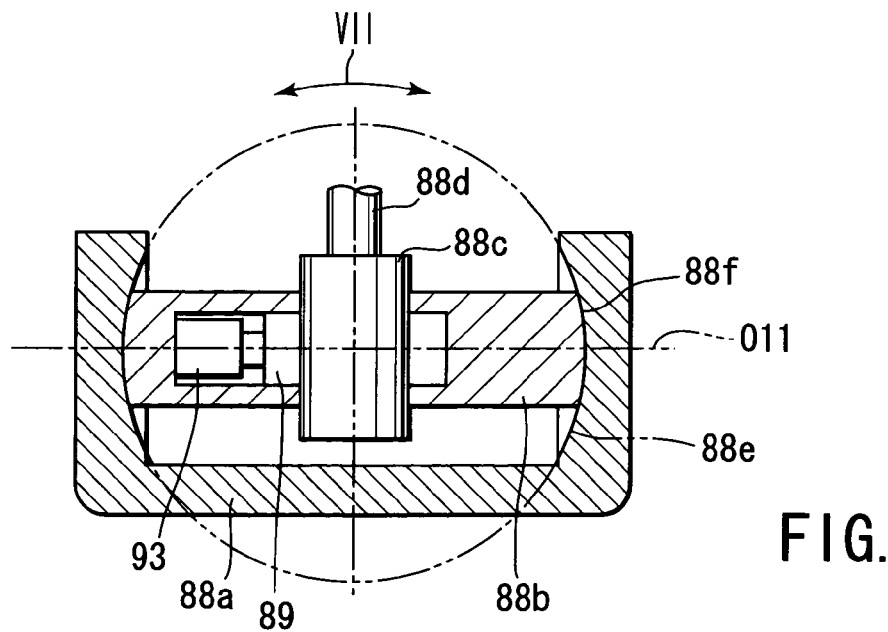
FIG. 7 is a schematic sectional view of the universal joint portion of the holding apparatus of the third embodiment, taken in the direction of arrow Z in FIG. 6.

As shown in FIG. 7, an encoder 93 is fixed in the shaft member 88b so as to be located on its central axis O11. The encoder 93 serves as a detecting mechanism that detects the angle of rotation of the wheel 88c with respect to the shaft member 88b. The input shaft of the encoder 93 is mounted on the axis O11 at a central portion 89 of the wheel 88c. The encoder 93 is connected to an arithmetic circuit (not shown), which computes the tilt angle of the wheel 88c, that is, the angle of inclination of the grip 70 to the shaft member 88b, from the rotating angle of the wheel 88c that is obtained by means of the encoder 93.

Figure 8:
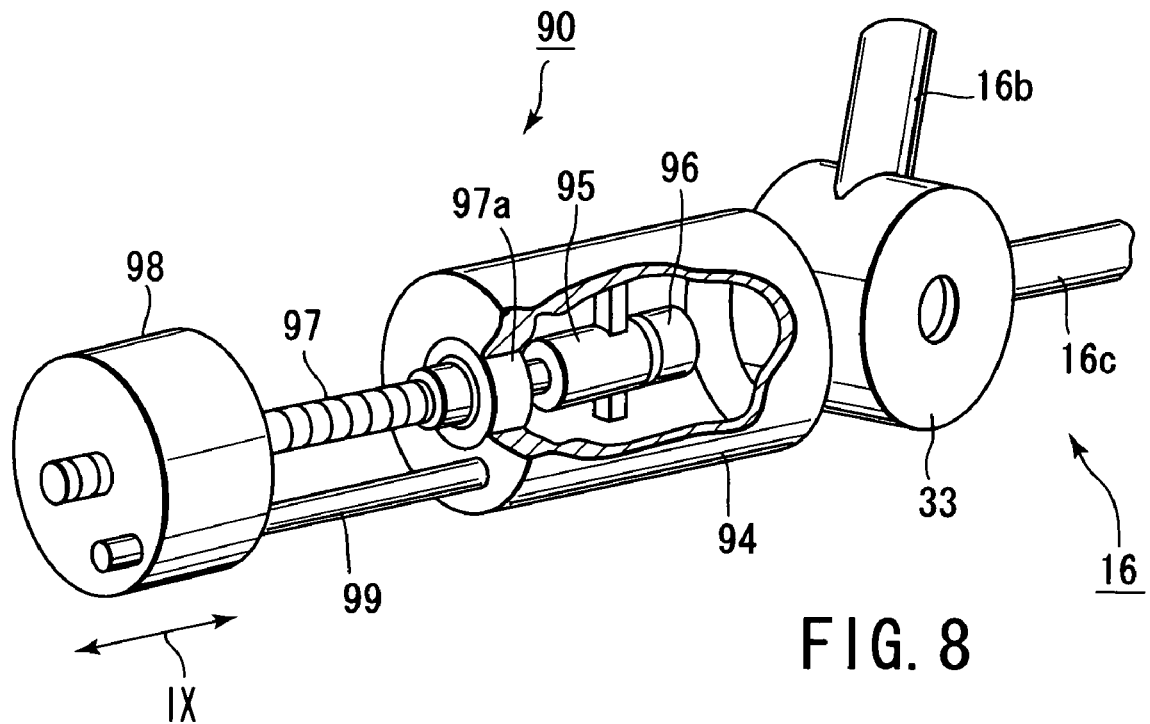
FIG. 8 is a schematic view showing the configuration of a counterweight adjusting mechanism located outside a parallelogrammatic link mechanism of the holding apparatus of the third embodiment.

The configuration of the counterweight adjusting mechanism 90 will now be described with reference to FIG. 8.

Outside a parallelogrammatic link mechanism 16, a motor housing 94 is mounted integrally on a third bearing 33 of the link mechanism 16. The motor housing 94 has therein a motor 95 that is coaxial with a third arm 16c. The motor 95 is fitted with an encoder 96 for detecting its rotational angle. The motor 95 is connected with a drive circuit (not shown) that applies a drive signal to the input of the motor 95 in response to an actuating signal from the arithmetic circuit. The encoder 96 is connected electrically to the arithmetic circuit in order to feed back the rotational angle of the motor 95. The motor 95 is attached integrally to a lead screw 97 that is supported on the motor housing 94 by means of the output shaft of the motor. As in the case of the second embodiment, a counterweight 98 is spirally fitted on the screw 97. The motor housing 94 and the counterweight 98 are detachably joined together. They are prevented from relative rotation by means of a guide 99 that is formed integrally with the housing 94.

When the motor housing 94 rotates as the motor 95 rotates, the counterweight 98 moves toward and away from the motor housing 94 along the guide 99. The motor 95 is connected to a drive circuit (not shown) that outputs a drive signal in accordance with a tilt angle $\beta$ that is calculated by the arithmetic circuit. In consequence, the necessary movement of the counterweight 98 is calculated by the arithmetic circuit, and an actuating signal is delivered to the drive circuit. The rotational angle of the motor 95 is detected by the encoder 96 and applied as required to the input of the arithmetic circuit. Thus, the arithmetic circuit ceases to deliver the actuating signal to the drive circuit when a required value is reached by the number of rotation of the motor 95. When the counterweight 98 reaches a position such that an increment of the rotation moment around the axis O2 that is caused by the increase of the weight W1 is corrected, the actuating signal from the drive circuit is stopped, whereupon the motor 95 ceases to rotate.

The following is a description of the operation of the medical instrument holding apparatus 10 constructed in this manner.

As in the case of the second embodiment, the operator manipulates the grip 70 to locate and fix the endoscope 75 in the desired position. The universal joint 88 is operated with the first to fifth electromagnetic brakes 54 to 58 unlocked to effect fine position adjustment of the distal end portion of the endoscope 75. More specifically, the grip 70 is inclined in the direction of arrow VIII in FIG. 6 around the axis O11 and in the direction of arrow VII in FIG. 7. As the grip 70 tilts in the direction of arrow VIII, the wheel 88c rotates. When this is done, the grip 70 is supposed to be inclined at the angle $\beta$, as shown in FIG. 6, for example. The rotational angle $\beta$ is detected by means of the encoder 93 (see FIG. 7) in the shaft member 88b, and the resulting detection signal is delivered to the arithmetic circuit (not shown). In response to the input signal from the encoder 93, the arithmetic circuit calculates the angle $\beta$ of inclination of the grip 70 to the bearing portion 88a.

Figure 9:
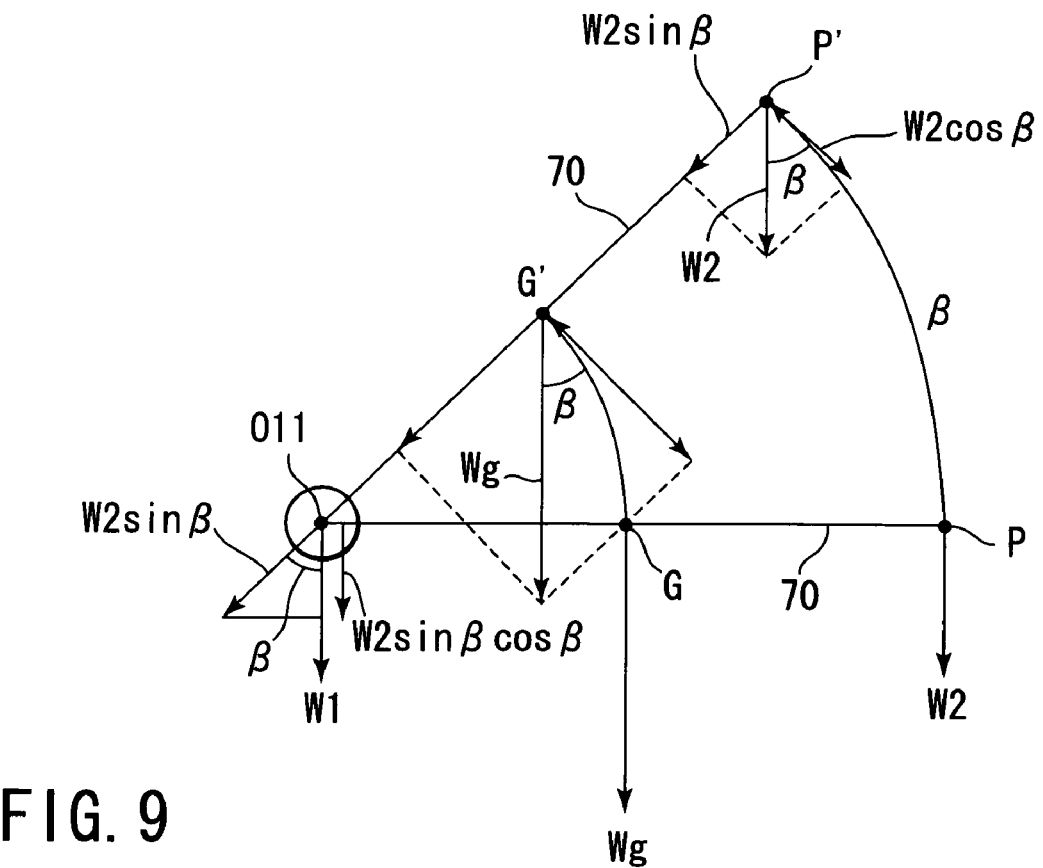
FIG. 9 is a schematic representation showing illustrating the change of weight that is generated when a grip of the holding apparatus of the third embodiment is inclined.

Referring now to FIG. 9, there will be described the change of the weight W1 on the bearing portion 88a that is caused when the supporting member 88d is inclined at the angle $\beta$ with respect to the bearing portion 88a.

When the supporting member 88d of the bearing portion 88a is inclined at the angle $\beta$ to its vertical position, the unbalance weight W2 at the point P of action or the endoscope manipulating point of the grip 70 is divided into two components of force. The components consist of a parallel component that acts in a direction parallel to the grip 70 (or the longitudinal direction of the body portion 70a of the grip 70) when the supporting member 88d is located upright and a vertical component that acts at right angles to the parallel direction. Thus, the vertical component W2·cos $\beta$ is used as the unbalance force around the central axis O11 that is conducive to the moment around the axis O11 when the grip 70 is inclined at the angle $\beta$. The parallel component W2·sin $\beta$, a force parallel to the grip 70, acts at right angles to the axis O11. A component W2·sin $\beta$·cos $\beta$ that acts at right angles to the parallel component W2·sin $\beta$ serves as a weight that acts in the same direction with the weight W1 on the central axis O11, that is, a force to generate the rotation moment around the axis O2 of rotation. The weight W1 that then acts on the universal joint 88 is a force resultant from the components. If the resultant force is W1$\beta$, it is given by W1$\beta$=W1+W2·sin $\beta$·cos $\beta$. The arithmetic circuit is stored with an increment of the weight W1 for the tilt angle $\beta$, and the resulting increment of the rotation moment around the axis O2 of rotation is calculated by the arithmetic circuit. Thus, the necessary movement of the counterweight 98 is calculated by the arithmetic circuit, and an actuating signal is delivered to the drive circuit. In response to the input of the actuating signal, the drive circuit delivers a drive signal to the motor 95. If the motor 95 is driven, the lead screw 97 rotates with the aid of a bearing 97*a*. Since the counterweight 98 that is spirally fitted on the screw 97 is restrained from rotating by the guide 99, the counterweight 98 moves in S the direction of arrow IX.

The rotational angle of the motor 95 is detected by means of the encoder 96, and the resulting detection signal is transmitted from the arithmetic circuit to drive circuit. A signal for precalculated revolutions of the motor 95 is delivered to the drive circuit through the arithmetic circuit. The drive circuit controls the drive signal for the motor 95. When the counterweight 98 is located in a position such that the apparatus 10 is balanced, the motor 95 ceases to rotate.

According to this embodiment described above, the following effects can be obtained.

Since the position of the counterweight 98 can be automatically corrected if the rotation moment around the axis O2 changes as the grip 70 tilts, the endoscope 75 never fails to operate in a balanced state. Thus, the endoscope 75 can be balanced at any time as it is inched, so that its manipulation is easy and stable.

To cope with the dislocation of the point P of action that is caused by the difference in the grip holding direction, as described in connection with the second embodiment, the arithmetic circuit is also programmed in advance with reference positions that match varied holding styles, for example. Thereupon, the position of the counterweight 98 can be corrected in like manner by alternatively inputting holding positions.

With use of the medical instrument holding apparatus 10, therefore, restrictions on the observation of the site of operation and the operating space for the medical instrument 75 can be minimized. Thus, the instrument 75 can be moved, located, and fixed easily and securely, so that its fine manipulation, for example, can be stabilized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical instrument holding apparatus comprising:
a medical instrument;
a supporting mechanism which has a distal end portion supporting the medical instrument and a holding portion being held by the operator;
a moving mechanism which has first and second sides and which supports the supporting mechanism;
a shaft portion located between the first and second sides and allowing the medical instrument and the supporting mechanism to be rotated about the shaft portion;
a basal portion which is coupled to the shaft portion, the basal portion supporting the moving mechanism and allowing the moving mechanism to rotate about the shaft portion;
a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and
a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;
wherein:
the moving mechanism and the supporting mechanism have braking mechanisms capable of being switched between a restrictive state in which the moving and supporting mechanisms are prevented from moving and a permissive state in which the mechanisms are allowed to move, and the supporting mechanism has a switch which is operated by an operator and switches the braking mechanisms to switch the moving and supporting mechanisms between the restrictive state and the permissive state;
the holding portion is located so that a combined center of gravity of the holding portion and the medical instrument and the center of operation by the operator are situated in different positions on the holding portion; a center of inclination of the ball joint around which the holding portion is inclined by means of the ball joint being situated in a position different from the combined center of gravity of the holding portion and the medical instrument and the supporting mechanism further includes a support arm having a first end and a second end, the first end being supported on the moving mechanism;
the moving mechanism has a parallelogrammatic link mechanism, the link mechanism including: a first arm having first and second arm ends, the first arm end being connected to the support arm; a second arm having third and fourth arm ends, the third arm end being rotatably connected to the first arm end of the first arm, the second arm being coupled to the shaft portion between the third and fourth arm ends of the second arm to support the moving mechanism for rotating motion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the fifth arm end of the third arm so as to be parallel to the first arm, the counterweight being located on the eighth arm end of the fourth arm;
the first arm is shorter than the fourth and second arms;
the counterweight has an adjusting mechanism which adjusts the position of the center of gravity of the counterweight along the axis of the fourth arm; and
the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

2. A medical instrument holding apparatus comprising:
a medical instrument;
a supporting mechanism which has a distal end portion supporting the medical instrument and a holding portion being held by the operator;
a moving mechanism which has first and second sides and which supports the supporting mechanism;
a shaft portion located between the first and second sides and allowing the medical instrument and the supporting mechanism to be rotated about the shaft portion;
a basal portion which is coupled to the shaft portion, the basal portion supporting the moving mechanism and allowing the moving mechanism to rotate about the shaft portion;
a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and
a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;
wherein:
the moving mechanism and the supporting mechanism have braking mechanisms capable of being switched between a restrictive state in which the moving and supporting mechanisms are prevented from moving and a permissive state in which the mechanisms are allowed to move, and the supporting mechanism has a switch which is operated by an operator and switches the braking mechanisms to switch the moving and supporting mechanisms between the restrictive state and the permissive state;
the holding portion is located so that a combined center of gravity of the holding portion and the medical instrument and the center of operation by the operator are situated in different positions on the holding portion; a center of inclination of the ball joint around which the holding portion is inclined by means of the ball joint being situated in a position different from the combined center of gravity of the holding portion and the medical instrument and the supporting mechanism further includes a support arm having a first end and a second end, the first end being supported on the moving mechanism;
the moving mechanism has a parallelogrammatic link mechanism, the link mechanism including: a first arm having first and second arm ends, the first arm end being connected to the support arm; a second arm having third and fourth arm ends, the third arm end being rotatably connected to the first arm end of the first arm, the second arm being coupled to the shaft portion between the third and fourth arm ends of the second arm to support the moving mechanism for rotating motion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the fifth arm end of the third arm so as to be parallel to the first arm, the counterweight being located on the eighth arm end of the fourth arm;
the counterweight has an adjusting mechanism which adjusts the position of the center of gravity of the counterweight along the axis of the fourth arm; and
the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

3. A medical instrument holding apparatus comprising:
a supporting mechanism which has a distal end portion supporting a medical instrument and a holding portion being held by the operator;
a moving mechanism which has first and second sides and which supports the supporting mechanism;
a shaft portion located between the first and second sides and allowing the medical instrument and the supporting mechanism to be rotated about the shaft portion;
a basal portion which is coupled to the shaft portion, the basal portion supporting the moving mechanism and allowing the moving mechanism to rotate about the shaft portion;
a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and
a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;
wherein:
the moving mechanism and the supporting mechanism have braking mechanisms capable of being switched between a restrictive state in which the moving and supporting mechanisms are prevented from moving and a permissive state in which the mechanisms are allowed to move, and the supporting mechanism has a switch which is operated by an operator and switches the braking mechanisms to switch the moving and supporting mechanisms between the restrictive state and the permissive state;
the moving mechanism has a parallelogrammatic link mechanism, the link mechanism including: a first arm having first and second arm ends, the first arm being supported on the supporting mechanism; a second arm having third and fourth arm ends, the third arm end being rotatably connected to the first arm end of the first arm, the second arm being coupled to the shaft portion between the third and fourth arm ends of the second arm to support the moving mechanism for rotating motion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the third arm so as to be parallel to the first arm, the fourth arm having the counterweight on the eighth arm end thereof;

the first arm is shorter than the fourth and second arms;

the counterweight has an adjusting mechanism which adjusts the position of the center of gravity of the counterweight along the axis of the fourth arm; and the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

4. A medical instrument holding apparatus comprising:

a supporting mechanism which has a distal end portion supporting a medical instrument and a holding portion being held by the operator;

a moving mechanism which has first and second sides and which supports the supporting mechanism;

a shaft portion located between the first and second sides and allowing the medical instrument and the supporting mechanism to be rotated about the shaft portion;

a basal portion which is coupled to the shaft portion, the basal portion supporting the moving mechanism and allowing the moving mechanism to rotate about the shaft portion;

a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;

wherein:

the moving mechanism and the supporting mechanism have braking mechanisms capable of being switched between a restrictive state in which the moving and supporting mechanisms are prevented from moving and a permissive state in which the mechanisms are allowed to move, and the supporting mechanism has a switch which is operated by an operator and switches the braking mechanisms to switch the moving and supporting mechanisms between the restrictive state and the permissive state;

the moving mechanism has a parallelogrammatic link mechanism, the link mechanism including: a first arm having first and second arm ends, the first arm being supported on the supporting mechanism; a second arm having third and fourth arm ends, the third arm end being rotatably connected to the first arm end of the first arm, the second arm being coupled to the shaft portion between the third and fourth arm ends of the second arm to support the moving mechanism for rotating motion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the third arm so as to be parallel to the first arm, the fourth arm having the counterweight on the eighth arm end thereof;

the counterweight has an adjusting mechanism which adjusts the position of the center of gravity of the counterweight along the axis of the fourth arm; and the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

5. A medical instrument holding apparatus comprising:

a medical instrument;

a supporting mechanism which has a distal end portion supporting the medical instrument and a holding portion being held by the operator;

a moving mechanism which has first and second sides and which supports the supporting mechanism;

a shaft portion located between the first and second sides and allowing the medical instrument and the supporting mechanism to be rotated about the shaft portion;

a basal portion which is coupled to the shaft portion, the basal portion supporting the moving mechanism and allowing the moving mechanism to rotate about the shaft portion;

a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;

wherein:

the holding portion is located so that a combined center of gravity of the holding portion and the medical instrument and the center of operation by the operator are situated in different positions; a center of inclination of the ball joint around which the holding portion is inclined by means of the ball joint being situated in a position different from the center of gravity of a heavy structure including the holding portion and the medical instrument and the supporting mechanism further includes a support arm having a first end and a second end, the first end being supported on the moving mechanism and the second end supporting the ball joint;

the moving mechanism has a parallelogrammatic link mechanism, the link mechanism including: a first arm having first and second arm ends, the first arm end being connected to the support arm; a second arm having third and fourth arm ends, the third arm end being rotatably connected to the first arm end of the first arm, the second arm being coupled to the shaft portion between the third and fourth arm ends of the second arm to support the moving mechanism for rotating motion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the fifth arm end of the third arm so as to be parallel to the first arm, the counterweight being located on the eighth arm end of the fourth arm;

the first arm is shorter than the fourth and second arms;

the counterweight has an adjusting mechanism which adjusts the position of the center of gravity of the counterweight along the axis of the fourth arm; and the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

6. A medical instrument holding apparatus comprising:

a medical instrument;

a supporting mechanism which has a distal end portion supporting the medical instrument and a holding portion being held by the operator;

a moving mechanism which has first and second sides and which supports the supporting mechanism;

a shaft portion located between the first and second sides and allowing the medical instrument and the supporting mechanism to be rotated about the shaft portion;

a basal portion which is coupled to the shaft portion, the basal portion supporting the moving mechanism and allowing the moving mechanism to rotate about the shaft portion;

a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;

wherein:

the holding portion is located so that a combined center of gravity of the holding portion and the medical instrument and the center of operation by the operator are situated in different positions; a center of inclination of the ball joint around which the holding portion is inclined by means of the ball joint being situated in a position different from the center of gravity of a heavy structure including the holding portion and the medical instrument and the supporting mechanism further includes a support arm having a first end and a second end, the first end being supported on the moving mechanism and the second end supporting the ball joint;

the moving mechanism has a parallelogrammatic link mechanism, the link mechanism including: a first arm having first and second arm ends, the first arm end being connected to the support arm; a second arm having third and fourth arm ends, the third arm end being rotatably connected to the first arm end of the first arm, the second arm being coupled to the shaft portion between the third and fourth arm ends of the second arm to support the moving mechanism for rotating motion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the fifth arm end of the third arm so as to be parallel to the first arm, the counterweight being located on the eighth arm end of the fourth arm;

the counterweight has an adjusting mechanism which adjusts the position of the center of gravity of the counterweight along the axis of the fourth arm; and the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

7. A medical instrument holding apparatus comprising:

a supporting mechanism which has a distal end portion supporting a medical instrument and a holding portion being held by the operator;

a moving mechanism which has first and second sides and which supports the supporting mechanism;

a shaft portion located between the first and second sides and allowing the medical instrument and the supporting mechanism to be rotated about the shaft portion;

a basal portion which is coupled to the shaft portion, the basal portion supporting the moving mechanism and allowing the moving mechanism to rotate about the shaft portion;

a ball joint located between the moving mechanism and the supporting mechanism to operatively connect the moving mechanism and the supporting mechanism, the ball joint being provided in a position shifted from a center of gravity of the holding portion on the supporting mechanism toward the moving mechanism, the ball joint further supporting the supporting mechanism to be pivotable with respect to the moving mechanism; and a counterweight which is located on the second side of the moving mechanism such that a first rotation moment is smaller than a second rotation moment generated from the weights of the medical instrument and the supporting mechanism, the counterweight acting about the shaft portion in the opposite direction to the second rotation moment;

wherein:

the moving mechanism has a parallelogrammatic link mechanism, the link mechanism including: a first arm having first and second arm ends, the first arm end being supported on the supporting mechanism; a second arm having third and fourth arm ends, the third arm end being rotatably connected to the first arm end of the first arm, the second arm being coupled to the shaft portion between the third and fourth arm ends of the second arm to support the moving mechanism for rotating motion, and coupled to the basal portion by means of the shaft portion; a third arm kept parallel to the second arm and having fifth and sixth arm ends, the sixth arm end being connected to the second arm end of the first arm; and a fourth arm having seventh and eighth arm ends, the seventh arm end being connected to the fourth arm end of the second arm and the eighth arm end being connected to the third arm so as to be parallel to the first arm, the fourth arm having the counterweight on the eighth arm end thereof;

the first arm is shorter than the fourth and second arms;

the counterweight has an adjusting mechanism which adjusts the position of the center of gravity of the counterweight along the axis of the fourth arm; and the ball joint includes a detecting mechanism which detects the angle of inclination of the holding portion to the moving mechanism, and the adjusting mechanism includes an arithmetic mechanism which calculates the variation of the rotation moment around the shaft portion, based on the angle of inclination of the holding portion detected by means of the detecting mechanism, and a barycenter position adjusting mechanism which moves the counterweight along the axis of the fourth arm, thereby adjusting the position of the center of gravity of the counterweight, in accordance with the result of computation by the arithmetic mechanism.

* * * * *